United States Patent [19]

Lodge

[11] Patent Number: 5,462,726
[45] Date of Patent: Oct. 31, 1995

[54] METHOD OF INHIBITING SIDE EFFECTS OF SOLVENTS CONTAINING RICINOLEIC ACID OR CASTOR OIL OR DERIVATIVES THEREOF EMPLOYING A THROMBOXANE $A_2$ RECEPTOR ANTAGONIST AND PHARMACEUTICAL COMPOSITIONS CONTAINING SUCH SOLVENTS

[75] Inventor: Nicholas J. Lodge, Hamilton Square, N.J.

[73] Assignee: Bristol-Myers Squibb Company, Princeton, N.J.

[21] Appl. No.: 168,348

[22] Filed: Dec. 17, 1993

[51] Int. Cl.[6] .................................................. A61K 49/00
[52] U.S. Cl. ...................... 514/558; 514/559; 514/560; 514/561; 514/562; 514/563; 514/529; 514/922
[58] Field of Search .............................. 424/10; 514/558, 514/559, 560, 561, 562, 563, 529

[56] References Cited

U.S. PATENT DOCUMENTS 5,021,448  6/1991  Piraino et al. ........................ 514/415

OTHER PUBLICATIONS

Finn et al., CA 109:122162, "Influence of the rate of infusion on CsA niphrotoxicity in the rat", *Renal Failure*, vol. 11(1), pp. 3–15, 1988.

Racusen et al., CA 106:149103, "Early renal pathophysiology in an acute model of cyclosporine nephrotoxicity in rats", *Renal Failure*, vol. 10(1), pp. 29–37, 1987. Abstracts only.

Martindale, The Extra Pharmacopoeia, 29th Edition, 1989, London, The Pharmaceutical Press.

Martindale, The Extra Pharmacopoeia, 30th Edition, 1993, London, The Pharmaceutical Press.

J. of the American Society of Nephrology, Sep. 1993, vol. 4, No. 3.

Transplantation, Nov. 1991, 52(5), pp. 873–878, ISSN 0041-1337.

*Primary Examiner*—Raymond Henley, III
*Assistant Examiner*—Keith MacMillan
*Attorney, Agent, or Firm*—Burton Rodney

[57] ABSTRACT

A method is provided for inhibiting or preventing toxicity and other unwanted effects (a) caused by solvents for pharmaceuticals which solvents contain castor oil or ricinoleic acid or derivatives thereof, such as Cremophor, or (b) caused by a drug, such as cyclosporine A, dissolved or suspended in solvents such as ricinoleic acid or castor oil or derivative thereof, employing a thromboxane $A_2$ receptor antagonist. Solvent compositions containing ricinoleic acid or castor oil or derivatives thereof and a thromboxane $A_2$ receptor antagonist, and pharmaceutical compositions including a drug, solvent containing ricinoleic acid or castor oil or derivative thereof, and a thromboxane $A_2$ receptor antagonist are also provided.

10 Claims, 4 Drawing Sheets

METHOD OF INHIBITING SIDE EFFECTS OF SOLVENTS CONTAINING RICINOLEIC ACID OR CASTOR OIL OR DERIVATIVES THEREOF EMPLOYING A THROMBOXANE A$_2$ RECEPTOR ANTAGONIST AND PHARMACEUTICAL COMPOSITIONS CONTAINING SUCH SOLVENTS

FIELD OF THE INVENTION

The present invention relates to a method for inhibiting or preventing toxicity and other unwanted side effects caused by pharmaceutical solvents containing ricinoleic acid or castor oil or a derivative thereof, such as Cremophor EL, and by pharmaceuticals dissolved or suspended in such solvents, employing a thromboxane A$_2$ receptor antagonist, and to solvent compositions containing a thromboxane A$_2$ receptor antagonist, and to pharmaceutical compositions including a drug, solvents containing ricinoleic acid or castor oil or a derivative thereof and a thromboxane A$_2$ receptor antagonist.

BACKGROUND OF THE INVENTION

Ricinoleic acid, castor oil or derivatives thereof have been employed as effective solvents or carriers for pharmaceuticals. Unfortunately such solvents have been found to have untoward side effects. For example, ricinoleic acid and castor oil and solvents containing these substances, such as Cremophor, cause vasoconstriction. It has been found that Cremophor (a derivative of castor oil and ethylene oxide) evokes a concentration-dependent increase in force development in vascular tissues, such as the jugular vein and aorta.

Cremophor EL is known for its use with an extensive array of pharmaceuticals including taxol (Rowinsky et al "Taxol: The First of the Taxanes, an Important New Class of Antitumor Agents, Seminars in Oncology, Vol. 19, No. 6 (December) 1992, 646–662), miconazole (Handbook on Injectable Drugs), echinomycin (Handbook on Injectable Drugs), teniposide (Rowinsky et al supra), vitamin K (Rowinsky et al supra), didemnin B (Rowinsky et al supra), diazepam (Lau et al, "Absorption of diazepam and lorazepam following intranasal administration", Int. J. Pharm. 54:171–174 (Sep. 1) 1989), althesin (Dye et al, Br. Med. J. 280:1353 (Jun. 7) 1980).

The side effects caused by use of solvents such as Cremophor or other solvents containing ricinoleic acid and/or castor oil or derivatives thereof may be compounded by the particular drug dissolved in or otherwise carried by such solvent.

Cyclosporine A (CsA) is a cyclic polypeptidic immunosuppressive agent that is widely used in organ transplantation and for the treatment of autoimmune disease. Unfortunately, the use of this agent is frequently associated with renal toxicity and hypertension (Myers et al, "Cyclosporine A associated chronic nephropathy", N. Eng. J. Med. 311: 699–705, 1984; Loughran et al, "Incidence of hypertension after marrow transplantation among 112 patients randomized to either CsA or methotrexate as graft-versus-host-disease prophylaxis", Br. J. Haematol. 59: 547–553, 1985). CsA has been shown to produce vasoconstriction in the isolated perfused kidney (Mehring et al, "Mechanisms of CsA-induced vasoconstriction in the isolated perfused rat kidney", Nephron 60: 447–481, 1992) and to increase the sensitivity of isolated blood vessels and cultured vascular smooth muscle cells (Lamb and Webb, "Cyclosporine A augments reactivity of isolated blood vessels", Life Sci. 40: 2571–2578, 1987; Bokenmeyer et al, "Atrial natriuretis peptide blunts the cellular effects of cyclsporine in smooth muscle", Hypertension 21: 166–172, 1993) to a variety of stimuli. Adrenergic mechanisms (Mehring et al, supra, Tronc et al, "Mechanism of hind-limb vasoconstriction due to cyclosporin A in the dog", Circ. Res. 71: 1159–1164, 1992) and increased levels of endothelin (Fogo et al, "Endothelin receptor antagonism is protective in in vivo acute cyclosporine toxicity", Kidney Intl. 42: 770–774, 1992; Takeda et al, "Endothelin-1 receptor antagonist: effects on endothelin- and cyclosporine-treated mesangial cells", Kidney Int. 42: 1713–1719, 1992) have recently been proposed to play a role in the CsA-induced toxicity. When given by infusion, CsA is prepared in Cremophor and then diluted in saline prior to administration.

DESCRIPTION OF THE INVENTION

In accordance with the present invention, a method is provided for inhibiting or preventing unwanted side effects caused by a pharmaceutical solvent containing ricinoleic acid or castor oil or a derivative thereof, such as Cremophor EL, employing a thromboxane A$_2$ receptor antagonist in conjunction with such solvent.

In another embodiment of the method of the invention, the thromboxane A$_2$ receptor antagonist is employed in conjunction with a pharmaceutical composition including a pharmaceutical, such as cyclosporine A, and a solvent containing ricinoleic acid or castor oil or a derivative thereof.

In a preferred embodiment the pharmaceutical composition includes a drug such as cyclosporine A or taxol in Cremophor EL.

In a further embodiment of the present invention a solvent formulation is provided formed of a solvent containing ricinoleic acid or castor oil or a derivative thereof and a thromboxane A$_2$ receptor antagonist.

A preferred solvent formulation in accordance with the present invention is Cremophor EL and the thromboxane A$_2$ receptor antagonist BMS 180,291.

In still another embodiment of the present invention, a pharmaceutical composition is provided which includes a pharmaceutical;

a solvent containing ricinoleic acid or castor oil or a derivative thereof; and a thromboxane A$_2$ receptor antagonist.

A preferred formulation is where the pharmaceutical is cyclosporine A or taxol, the solvent is Cremophor EL, and the thromboxane A$_2$ receptor antagonist is BMS 180,291.

Examples of solvents including ricinoleic acid or derivatives thereof, or castor oil or derivatives thereof suitable for use herein include, but are not limited to, Cremophor or Cremophor EL, castor oil, ricinoleic acid, polyoxyl 35 castor oil, polyethoxylated castor oils or the triricinoleate ester of ethoxylated glycerol with macrogol ricinoleate and the corresponding free glycols.

The term "Cremophor" or "Cremophor EL" as employed herein refers to polyoxyethylated castor oil that may or may not contain alcohol, such as ethanol, and is marketed by BASF and as Etocas by Croda, U.K. It is principally composed of the triricinoleate ester of ethoxylated glycerol with smaller amounts of macrogol ricinoleate and the corresponding free glycols.

The term "castor oil" as employed herein refers to a solvent composed principally of ricinoleic acid and derivatives thereof.

Pharmaceuticals which may be present in the pharmaceutical compositions of the invention carried in the solvent containing ricinoleic acid or castor oil or derivatives thereof include, but are not limited to, cyclosporine A, vitamin K (phytonadione, konakion), teniposide, didemnin B, miconazole, diazepam, althesin, taxol, echinomicin, and the like.

The above pharmaceuticals are known in the art and are employed in amounts as set out in the Physicians' Desk Reference (PDR), 47th Ed. 1993. If a particular pharmaceutical is not set out in the PDR, it will be employed in amounts set out in publications and/or patents relating thereto.

Thromboxane $A_2$ receptor antagonists which may be employed herein include the 7-oxabicycloheptane and 7-oxabicycloheptene compounds disclosed in U.S. Pat. No. 4,537,981 to Snitman et al, especially [1S-[1α,2α,(Z), 3α(1E,3S*,4R*),4α]]-7-[3-(3-hydroxy- 4-phenyl-1-pentenyl)-7-oxabicyclo[2.2.1]hept-2-yl]-5-heptenoic acid (SQ 29,548); the 7-oxabicycloheptane substituted aminoprostaglandin analogs disclosed in U.S. Pat. No. 4,416,896 to Nakane et al, especially, [1S-[1α,2α(Z) ,3α,4α]]-7-[3-[[2-(phenylamino)carbonyl] hydrazino]methyl]-7-oxabicyclo [2.2.1]-hept-2-5-heptenoic acid; the 7-oxabicycloheptane substituted diamide prostaglandin analogs disclosed in U.S. Pat. No. 4,663,336 to Nakane et al, especially, [1S-[1α, 2α(Z) ,3α,4α]]-7-[3-[[[[ (1-oxoheptyl) amino]acetyl]amino] methyl]-7-oxabicyclo-[ 2.2.1]hept-2-yl]-5-heptenoic acid (SQ30,741 which is preferred) and the corresponding tetrazole, and [1S[ 1α,2α(Z) ,3α,4α]]-7-[3-[[[[(4-cyclohexyl-1-oxobutyl) amino]acetyl]amino]-methyl]-7-oxabicyclo [2.2.1]hept-2-yl]-5-heptenoic acid; interphenylene 7-oxabicycloheptyl substituted heterocyclic amide prostaglandin analogs as disclosed in U.S. Pat. No. 5,100,889 to Misra et al, including [1S- [1α, 2α, 3α, 4α)]-2-[[3-[[4-(pentylamino) carbonyl]-2-oxazolyl]-7-oxabicyclo [2.2.1] hept-2-yl]-methyl] benzenepropanoic acid, sodium salt referred to as BMS 180,291 herein, which is most preferred, or esters or other salts thereof, [1S-(1α, 2α, 3α, 4α)]-2-[[3-[4-[[(4-cyclohexylbutyl) amino]-carbonyl] -2-oxazolyl]-7-oxabicyclo [2.2.1] hept-2-yl]methyl] benzenepropanoic acid, (SQ 33,961) which is also preferred, or esters or salts thereof; [1S(1α, 2α,3α, 4α)]-2-[[3-[4-[[(4-chlorophenyl)butyl]-amino] carbonyl]-2-oxazolyl]-7-oxabicyclo [2.2.1] hept-2-yl]methyl] benzenepropanoic acid or esters, or salts thereof; [1S-(1α, 2α,3α,4α)]-3-[[3-[4-[[(4-cyclohexylbutyl) amino]carbonyl] -2-oxazolyl]-7-oxabicyclo-[ 2.2.1]hept-2-yl]methyl] benzeneacetic acid, or esters or salts thereof; [1S-(1α,2α, 3α,4α)]-2-[[3-[4-[[(4-cyclohexylbutyl) amino]carbonyl]-2-oxazolyl]-7-oxabicyclo[ 2.2.1] hept-2 -yl]methyl]phenoxy] acetic acid, or esters or salts thereof; [1S-( 1α, 2α, 3α, 4α)]-2- [[3-[4-[[(7,7-dimethyloctyl)amino]-carbonyl] -2 -oxazolyl]-7-oxabicyclo [2.2.1] hept-2-yl]methyl] benzenepropanoic acid, or esters or salts thereof; 7-oxabicycloheptyl substituted heterocyclic amide prostaglandin analogs as disclosed in U.S. Pat. No. 5,100,889 to Hall et al, including [1S[ 1α,2α(Z) ,3α, 4α]]-6-[3-[4-[[(4-cyclohexylbutyl)-amino] carbonyl]-2-oxazolyl]-7-oxabicyclo [2.2.1] hept- 2-yl]-4-hexenoic acid, or esters or salts thereof; [1S-[1α,2α(Z) ,3α, 4α]]-6-[3-[4-[[(4-cyclohexylbutyl)-amino] carbonyl]-2-thiazolyl]-7-oxabicyclo [2.2.1]hept- 2-yl]-4-hexenoic acid, or esters or salts thereof; 1S-[1α,2α(Z) ,3α, 4α]]-6-[3-[4-[[(4-cyclohexylbutyl)methylamino] carbonyl] -2 -oxazolyl]-7-oxabicyclo-[ 2.2.1]hept-2-yl]-4-hexenoic acid, or esters or salts thereof; [1S-[1α,2α(Z) ,3α,4α]]-6-[3-[4-[(4-cyclohexyl)-amino] carbonyl]-2-oxazolyl]-7-oxabicyclo[ 2.2.1]hept-2-yl]-4-hexenoic acid or esters or salts thereof; [1S-[1α,2α(Z) ,3α,4α]]-6-[3-[4-[[(4-(cyclohexylethyl)-amino] carbonyl]-2-oxazolyl]-7-oxabicyclo [2.2.1] hept- 2-yl]-4-hexenoic acid or esters or salts thereof; [1S-[1α,2α(Z) ,3α,4α]]-6-[3-[4-[[(2-chlorophenyl)-ethyl] amino]carbonyl]-2-oxazolyl]-7-oxabicyclo [2.2.1]hept-2-yl]-4-hexenoic acid, or esters or salts thereof; [1S-[1α, 2α(Z),3α,4α]-6-[3-[4-[[4-(4-chlorophenyl) amino]carbonyl]-2-oxazolyl]-7-oxabicyclo-[ 2.2.1]hept-2-yl]-4-hexenoic acid, or esters or salts thereof; [1S-[1α,2α(Z) ,3α,4α] ]-6-[3-[4-[[(4-chlorophenyl) amino]carbonyl]-2-oxazolyl]-7-oxabicyclo-[ 2.2.1]hept-2-yl]-4-hexenoic acid, or esters or salts thereof; [1S-[1α,2α(Z) ,3α,4α]]-6-[3-[4-[[[4- 4-chlorophenyl)butyl]amino]carbonyl]-2-oxazolyl]-7-oxabicyclo[ 2.2.1]hept-2-yl]-4-hexenoic acid, or esters or salts thereof; [1S-[1α, 2α(Z),3α,4α]]-6-[3-[ 4α- [[(6-cyclohexylhexyl)amino]carbonyl]-2-oxazolyl]- 7-oxabicyclo [2.2.1]hept-2-yl]-4-hexenoic acid, or esters, or salts thereof; [1S-[1α, 2α(Z),3α,4α]]-6-[3-[ 4-[[(6-cyclohexylhexyl)amino] carbonyl]-2-oxazolyl]- 7-oxabicyclo [2.2.1]hept-2-yl]-4-hexenoic acid, or esters or salts thereof; [1S-[1α, 2α(Z),3α, 4α]-6-[3-[ 4-[(propylamino)carbonyl]-2-oxazolyl]-7-oxabicyclo-[2.2.1] hept-2-yl]-4-hexenoic acid, or esters or salts thereof; [1S-[1α, 2α(Z),3α,4α]]-6-[3-[4-[[(4-butylphenyl) amino]carbonyl]-2-oxazolyl]-7-oxabicyclo[ 2.2.1]hept-2-yl]-4-hexenoic acid, or esters or salts thereof; [1S-[1α, 2α(Z),3α,4α]]-6-[3-[4-[(2,3-dihydro- 1H-indol-1-yl)carbonyl]-2-oxazolyl]-7-oxabicyclo [2.2.1]hept-2-yl]-4-hexenoic acid, or esters or salts thereof; [1S-[1α,2α(Z), 3α, 4α]]-6-[3-[ 4-[[(4-cyclohexylbutyl)amino]carbonyl]-2-oxazolyl]-7-oxabicyclo [ 2.2.1]hept-2-yl]-N-(phenylsulfonyl)-4-hexenamide; [1S-[1α, 2α(Z),3α,4α]]-6-[3-[4-[[(4-cyclohexylbutyl) amino]carbonyl]-2-oxazolyl]-N-(methylsulfonyl)-7-oxabicyclo [2.2.1]hept -2-yl]-4-hexenamide; [1S-[1α, 2α(Z),3α,4α]]-7-[3-[4-[[(4-cyclohexylbutyl) amino]carbonyl]-2-oxazolyl]-7- oxabicyclo[ 2.2.1]hept-2-yl]-5-heptenoic acid, or esters or salts thereof; [1S-[1α,2α(Z),3α,4α] ]-6-[3-[ 4-[[(4-cyclohexylbutyl)amino]carbonyl] -1H-imidazol- 2-yl]-7-oxabicyclo [2.2.1]hept-2-yl]-4-hexenoic acid or esters or salts thereof; [1S- [1α, 2α, 3α, 4α]]-6- [3-[ 4- [[(7,7-dimethyloctyl) amino]carbonyl] -2-oxazolyl]-7-oxabicyclo [2.2.1] hept-2-yl]-4-hexenoic acid, or esters or salts thereof; [1S-[1α,2α(E),3α,4α]]-6-[3-[ 4-[[(4-cyclohexylbutyl)amino]carbonyl]-2-oxazolyl] - 7-oxabicyclo [2.2.1]hept-2-yl] -4-hexenoic acid; [1S-[ 1α, 2α, 3α, 4α]]-3-[4-[[(4-cyclohexylbutyl) amino]-carbonyl]- 2-oxazolyl]-7-oxabicyclo [2.2.1]heptane-2-hexenoic acid or esters or salts thereof, with a preferred compound being [1S- [1α, 2α(Z),3α,4α]]-6-[3-[ 4-[[(4-cyclohexylbutyl)amino]carbonyl]-2-oxazolyl]- 7-oxabicyclo [2.2.1]hept-2-yl]-4-hexenoic acid or esters or salts thereof; 7-oxabicycloheptane imidazole prostaglandin analogs as disclosed in U.S. Pat. No. 4,977,174 including [1S-[ 1α,2α(Z),3α,4α]]-6-[3-[[4-(4-cyclohexyl-1-hydroxybutyl)- 1H-imidazol-1-yl]methyl]-7-oxabicyclo [2.2.1]hept-2-yl]-4-hexenoic acid or its methyl ester; [1S-[1α,2α(Z),3α,4α]]-6-[3-[[4-(3-cyclohexypropyl)- 1H-imidazol-1-yl]methyl]-7-oxabicyclo[ 2.2.1]hept-2-yl]-4-hexenoic acid or its methyl ester; [1S-[1α,2α(Z),3α, 4α]]-6-[3-[[4-(4-cyclohexyl- 1-oxobutyl)-1H-imidazol-1-yl]methyl]-7-oxabicyclo [2.2.1] hept-2-yl]-4-hexenoic acid or its methyl ester; [1S-[1α, 2α(Z),3α,4α]]-6-[3-(1H-imidazol- 1-ylmethyl]-7-oxabicyclo[2.2.1]hept-2-yl]-4-hexenoic acid or its methyl ester; or [1S-[ 1α,2α(Z) ,3α,4α]]-6-[3-[[4-[[ (4-cyclohexylbutyl)-amino] carbonyl]-1H-imidazol-1-yl]methyl]-7-oxabicyclo [2.2.1] hept-2-yl]-4-hexenoic acid or its methyl ester; the phenoxyalkyl carboxylic acids disclosed in U.S. Pat. No. 4,258,058 to Witte et al, especially 4-[2- (benzenesulfamido)ethyl]phenoxyacetic acid (BM 13,177—Boehringer Mannheim), the sulphonamidophenyl carboxylic acids disclosed in U.S. Pat. No. 4,443,477 to Witte et al, especially 4-[2-( 4-chlorobenzenesulfonamido)ethyl]phenylacetic acid (BM 13,505, Boehringer Mannheim), the arylthioalkylphenyl carboxylic acids disclosed in U.S. Pat. No. 4,752,616 especially 4-(3-((4-chlorophenyl)sulfonyl)-propyl)benzeneacetic acid.

Other examples of thromboxane $A_2$ receptor antagonists suitable for use herein include, but are not limited to (E)-5-[[[(pyridinyl)[3-(trifluoromethyl)phenyl] methylene] amino]oxy]pentanoic acid also referred to as R68,070— Janssen Research Laboratories, 3-[1-(4-chlorophenylmethyl)-5-fluoro-3-methylindol -2-yl]-2,2-dimethylpropanoic acid [(L-655240 Merck-Frosst) Eur. J. Pharmacol. 135(2):193, Mar. 17, 87], 5(Z)-7-(2,4,5-cis)-4-(2-hydroxyphenyl)- 2-trifluoromethyl-1,3-dioxan-5-yl)-heptenoic acid (ICI 185282, Brit. J. Pharmacol. 90 (Proc. Suppl):228 P-Abs., Mar. 87), 5(Z)-7-[2,2-dimethyl-4-phenyl-1,3-dioxan-cis- 5-yl]heptenoic acid (ICI 159995, Brit. J. Pharmacol. 86 (Proc. Suppl):808 P-Abs., Dec. 85), N,N'-bis[7-(3- chlorobenzeneamino-sulfonyl)-1,2,3,4-tetrahydro-isoquinol-yl] disulfonyl-imide (SKF 88046, Pharmacologist 25(3):116 Abs., 117 Abs. Aug. 83), 1α(Z)-2β,5α]-(+)-7-[5-[[(1,1'-biphenyl)-4-yl]-methoxy] 2-(4-morpholinyl)-3-oxo-cyclopentyl]-4-heptenoic acid (AH 23848 -Glaxo, Circulation 72(6):1208, Dec. 85, levallorphan allyl bromide (CM 32,191)); Sanofi, Life Sci. 31 (20–21):2261, Nov. 15, 82), (Z,2-endo-3-oxo)-7-(3-acetyl-2-bicyclo[2.2.1]-heptyl-5-hepta-3Z-enoic acid, 4-phenylthiosemi-carbazone (EP092); Univ. Edinburgh, Brit. J. Pharmacol. 84(3):595, March 85); GR 32,191—[1R-[ 1α(Z), 2β, 3β, 5α]]-(+)-7-[5-([1,1'-biphenyl]-4-ylmethoxy)- 3-hydroxy-2-(1-piperidinyl)cyclopentyl]-4-heptenoic acid; ICI 192,605-4 (Z) -6-[(2, 4,5-cis)2-chlorophenyl)- 4-(2-hydroxyphenyl)1,3-dioxan-5-yl] hexenoic acid; BAY u 3405 - 3-[[(4-fluorophenyl)-sulfonyl] amino]-1,2,3,4-tetrahydro-9H-carbazole-9-propanoic acid; or ONO 3708 -7- [2α, 4α-(dimethylmethano)- 6β-(2-cyclopentyl-2≠-hydroxyacetamido)-1α-cyclohexyl] -5 (Z) -heptenoic acid; (±) (5Z) -7- [3-endo-[ (phenylsulfonyl)amino]bicyclo [2.2.1]hept -2-exo-yl] heptenoic acid (S-145, Shionogi); (−)6,8-difluoro- 9-p-methylsulfonylbenzyl-1,2,3,4-tetrahydrocarbazol- 1-yl-acetic acid (L670596, Merck) and (3-[1-(4-chlorobenzyl)- 5-fluoro-3-methyl-indol-2-yl]2,2-dimethylpropanoic acid (L655240, Merck), and glyburide (also known as glibenclamide).

The disclosure of the above-mentioned U.S. patents and U.S. patent applications are incorporated herein by reference. The amounts of thromboxane $A_2$ receptor antagonist employed in the formulations of the invention will be set out in the above patents and patent applications.

The thromboxane $A_2$ receptor antagonist will be employed in the solvent formulation and pharmaceutical formulations of the invention in a weight ratio to the solvent of within the range of from about 0.0001:1 to about 10,000:1, preferably from about 0.003:1 to about 1000:1.

Where the pharmaceutical is present, the thromboxane $A_2$ receptor antagonist will be employed in a weight ratio to the pharmaceutical of within the range of from about 0.0001:1 to about 500:1, preferably from about 0.001:1 to about 250:1.

The formulations of the invention may also include additional solvents and/or carrier materials and/or extenders such as alcohols, e.g. ethanol, water, sodium chloride or dextrose or other pharmaceutically acceptable solvents used for systemic including oral or parenteral administration.

Preferred formulations of the invention will include the following:

|  | IV concentration |
| --- | --- |
| Thromboxane $A_2$ Receptor Antagonist | 1 to 10,000 mg/day |
| Cremorphor EL solvent Pharmaceutical | 10 to 20,000 mg/day concentration depends on particular drug used |

More preferred doses of the formulations of the invention are set out below.

| Thromboxane $A_2$ Receptor Antagonist BMS 180,291 | 2 to 1000 mg/day |
| --- | --- |
| Solvent Cremophor EL | 200 to 10,000 mg/day |
| Pharmaceutical Cyclosporine A | 10 to 1000 mg/day |

In carrying out the method of the present invention, the thromboxane $A_2$ antagonist in combination with the ricinoleic acid or castor oil or derivatives thereof and the pharmaceutical carried therein may be administered to mammalian species, such as monkeys, dogs, cats, rats, humans, etc., systemically, such as orally or parenterally (such as IV), as well as intraperitoneally, topically, or by intranasal administration, preferably by intravenous injection.

The thromboxane $A_2$ antagonist alone or with any of the other components of the formulation of the invention may be administered systematically, such as orally or parenterally, as well as locally to various arteries, preferably by intravenous injection.

With regard to dosage of thromboxane $A_2$ antagonist, where the drug is administered by catheter from about 0.1 to about 30 mg/kg/dose and preferably from about 0.5 to about 25 mg/kg/dose will be employed. From 1 to 5 doses per day will be required.

Where the thromboxane $A_2$ antagonist alone or in combination with any of the other components of the formulation of the invention is to be administered by angiography or intracoronary injection, it (or the combination) will be formulated in a conventional vehicle, such as distilled water, saline, Ringer's solution, or other conventional carriers.

The thromboxane $A_2$ antagonist alone or in combination with any of the other components of the formulation of the invention may also be incorporated in a conventional dosage form, such as a tablet, capsule or elixir or injectable. The above dosage forms will also include the necessary carrier material, excipient, lubricant, buffer, antibacterial, bulking agent (such as mannitol), anti-oxidants (ascorbic acid of sodium bisulfite) or the like. Parenteral dosage forms are preferred, although oral forms may be satisfactory as well.

The thromboxane $A_2$ antagonist may be employed in a separate dosage form from any of the other components of the formulation of the invention such as two separate injections or the two or three may be employed in a single dosage form, such as a single injection.

With regard to such systemic formulations, where the thromboxane $A_2$ antagonist is to be employed alone, single or divided doses of from about 1 to about 10,000 mg, preferably from about 2 to about 2000 mg/one to four times daily, may be administered in systemic dosage forms as described above.

With regard to combinations of the thromboxane $A_2$ antagonist with any of the other components of the formulation of the invention single or divided doses of from 2 to about 2000 mg of thromboxane $A_2$ antagonist, preferably 5 to 1500 mg thromboxane $A_2$ antagonist, may be administered one to four times daily.

The thromboxane $A_2$ antagonist alone or with any of the other components of the formulation of the invention may be administered prior to, during or after administration of the solvent and/or pharmaceutical.

Figure 1:
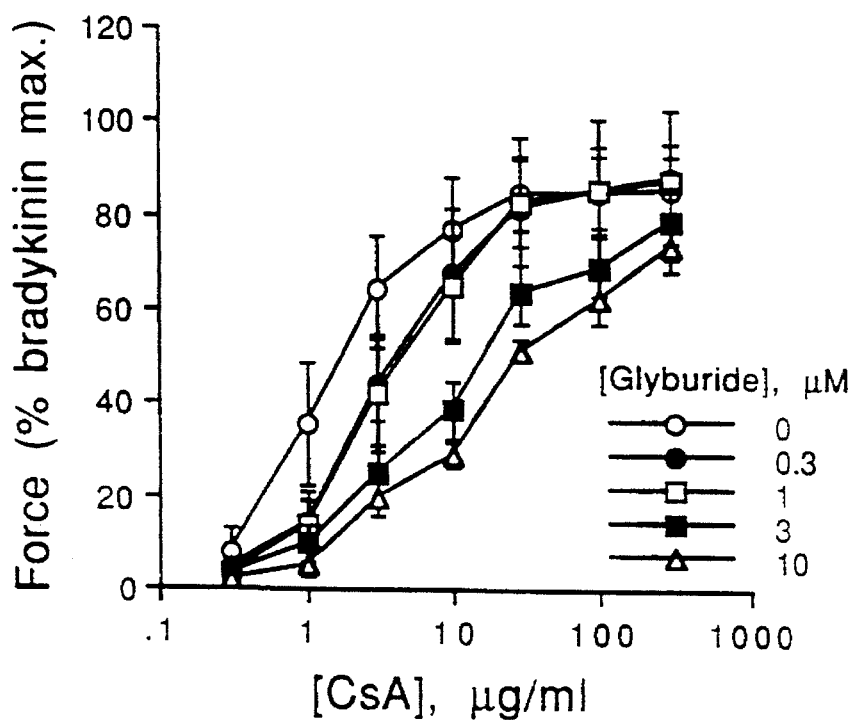
FIG. 1 is a graph showing effects of glyburide on CsA-induced force development in the jugular vein (n=4 for each group). CsA was dissolved in Cremophor. Force is expressed as a percentage of that generated by a maximally effective concentration of bradykinin.

The following Examples represent preferred embodiments of the present invention.

EXAMPLE 1

An injectable solution of Cremophor EL and the thromboxane $A_2$ receptor antagonist BMS 180,291, in accordance with the present invention, is set out below.

|  | Amount (mg) |
| --- | --- |
| BMS 180,291 | 150 |
| Cremophor EL | 5000 |
| Ethanol | 2100 (32.9%) |

The above injectable formultion was prepared by diluting the Cremophor EL with ethanol and saline, and then adding the thromboxane $A_2$ receptor antagonist BMS 180,291 with stirring.

The so prepared formulation of the invention when administered to a patient is substantially free of side effects normally attributable to Cremophor EL.

EXAMPLE 2

An injectable formulation of Cremophor EL and the thromboxane $A_2$ receptor antagonist SQ 30,741, in accordance with the present invention, is set out below.

|  | Amount (mg) |
| --- | --- |
| SQ 30,741 | 250 |
| Cremophor EL | 4500 |

The above injectable formulation was prepared by mixing the Cremophor EL diluted in saline, and SQ 30,741 with stirring.

The so-prepared formulation of the invention when administered to a patient is substantially free of side effects normally attributable to Cremophor EL.

EXAMPLE 3

An injectable formulation of castor oil and the thromboxane receptor antagonist SQ 29,548, in accordance with the present invention, is set out below.

|  | Amount (mg) |
| --- | --- |
| SQ 29,548 | 50 |
| Castor oil | 5000 |

The above injectable formulation was prepared by mixing the castor oil and SQ 29,548 with stirring.

The so-prepared formulation of the invention when administered to a patient is substantially free of side effects normally attributable to castor oil.

EXAMPLE 4

A pharmaceutical formulation in accordance with the present invention having the following composition was prepared as described below.

|  | Amount (mg) |
| --- | --- |
| Cyclosporine A (CsA) | 50 |
| BMS 180,291 | 150 |
| Cremophor EL | 650 |
| Ethanol | 278 (32.9%) |

The above injectable formulation was prepared by diluting the Cremophor EL with alcohol and then adding the cyclosporine A and BMS 180,291 and saline with stirring.

The so-prepared pharmaceutical formulation of the invention when administered to a patient is substantially free of side effects normally attributable to cyclosporine A and Cremophor EL.

EXAMPLE 5

A pharmaceutical formulation in accordance with the present invention having the following composition is prepared as described below.

|  | Amount (mg) |
|---|---|
| Cyclosporine A | 50 |
| Glyburide | 1000 |
| Ricinoleic acid | 600 |
| Ethanol | 280 |

The above injectable formulation was prepared by diluting the ricinoleic acid with ethanol and then adding the cyclosporine A and glyburide.

The so-prepared pharmaceutical formulation of the invention when administered to a patient is substantially free of side effects normally attributable to cyclosporine A and ricinoleic acid.

EXAMPLE 6

A thromboxane $A_2$ antagonist formulation suitable for oral administration for use in conjunction with Cremophor EL with or without a drug such as cyclosporine A, in accordance with the present invention, is set out below.

1000 tablets each containing 400 mg of thromboxane $A_2$ receptor antagonist were produced from the following ingredients.

| | |
|---|---|
| [1S-[1α,2α(Z),3α,4α]]-7-13-[[[[(1-Oxoheptyl)amino]acetyl]amino]methyl]-7-oxabicyclo[2.2.1]hept-2-yl]-5-heptenoic acid (SQ 30,741) | 400 g |
| Corn starch | 50 g |
| Gelatin | 7.5 g |
| Avicel (microcrystalline cellulose) | 25 g |
| Magnesium stearate | 2.5 g |

The thromboxane $A_2$ receptor antagonist (SQ30,741) and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of SQ30,741.

EXAMPLES 7 TO 12

Tablets for use in preventing or treating side effects caused by Cremophor EL are prepared as described in Example 6 except that the thromboxane $A_2$ receptor antagonist employed is [1S-[ 1α,2α(Z),3α,4α]]-7-[3-[[[[ (4-cyclohexyl-1-oxobutyl) amino]acetyl]amino]methyl]-7-oxabicyclo-[ 2.2.1]hept-2-yl]-5-heptenoic acid; GR 32,191; ICI 192, 605; R-68,070; BAY u 3405; or ONO 3708.

EXAMPLE 13

An injectable solution of thromboxane $A_2$ receptor antagonist for intravenous use in preventing or treating side effects caused by Cremophor EL is produced as follows.

| | |
|---|---|
| BMS 180,291 | 2500 mg |
| Methyl paraben | 5 mg |

| -continued | |
|---|---|
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 mL of solution.

EXAMPLE 14

An injectable for use in accordance with the present invention for treating and/or preventing side effects caused by ricinoleic acid is prepared as described in Example 7 except that the thromboxane $A_2$ receptor antagonist employed is the phenoxyalkyl carboxylic acid 4-[2-(benzenesulfamido)ethyl]-phenoxyacetic acid, disclosed in U.S. Pat. No. 4,258,058.

EXAMPLE 15

An injectable solution of thromboxane $A_2$ receptor antagonist for intravenous use for use in preventing or treating side effects caused by Cremophor EL, or solvents containing ricinoleic acid or castor oil or derivatives thereof, containing [1S-[ 1α,2α(Z) ,3α,4α]]-7-[3-[[[[(1-oxoheptyl)amino]-acetyl] amino]methyl]-7-oxabicyclo-[2.2.1]hept-2-yl]- 5-heptenoic acid (SQ 30,741) as the thromboxane $A_2$ receptor antagonist is prepared as described in Example 13.

EXAMPLE 16

An injectable solution of thromboxane $A_2$ receptor antagonist for intravenous use for use in preventing or treating side effects caused by Cremophor EL, or solvents containing ricinoleic acid or castor oil or derivatives thereof in accordance with the present invention is prepared as follows.

| | |
|---|---|
| [1S-(1α,2α,3α,4α)]-2-[[3-[4-[[(4-cyclohexylbutyl)amino]carbonyl]-2-oxazolyl]-7-oxabicyclo]2.2.1]hept-2-yl]methyl]benzenepropanoic acid (SQ 33,961) | 2500 mg |
| Methyl paraben | 5 mg |
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 mL of solution.

EXAMPLE 17

Tablets for use in accordance with the present invention are prepared as described in Example 1 except that the thromboxane $A_2$ receptor antagonist employed is [1S-[1α, 2α(Z),3α,4α]]-6-[3-[4-[[(4-cyclohexylbutyl) amino]carbonyl]-2-oxazolyl]-7-oxabicyclo [2.2.1] hept-2-yl]-4-hexenoic acid.

EXAMPLE 18

An injectable solution of thromboxane $A_2$ receptor antagonist for intravenous use containing [1S-[1α,2α(Z),3α,(1E,3S*,4R*)4α]]-7-[3-(3-hydroxy-4 -phenyl-1-pentenyl) -7-oxabicyclo [2.2.1]hept-2-yl]-5-heptenoic acid (SQ 29,548) as the thromboxane $A_2$ receptor antagonist for use in treating or preventing side effects caused by Cremophor EL, or solvents containing castor oil or ricinoleic acid or derivatives thereof, is prepared as described in Example 13.

EXAMPLE 19

A thromboxane $A_2$ antagonist formulation suitable for oral administration for use in treating or preventing side effects caused by Cremophor EL, or solvents containing castor oil or ricinoleic acid or derivatives thereof, is set out below.

1000 tablets each containing 40 mg of thromboxane $A_2$ receptor antagonist are produced from the following ingredients.

| | |
|---|---|
| SQ 33,961 | 40 g |
| Corn Starch | 50 g |
| Gelatin | 7.5 g |
| Avicel (Microcrystalline cellulose) | 25 g |
| Magnesium stearate | 2.5 g |

The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 40 mg of active ingredient.

EXAMPLE 20

The following experiments were carried out to examine the effects of cyclosporine A(CsA) and its vehicle, Cremophor EL on force development in isolated vascular smooth muscle and the effects of thromboxane $A_2$ receptor antagonists, glyburide and BMS 180,291 and the anti-inflammatory agent indomethacin on Cremophor-induced vasoconstriction.

BMS 180,291 refers to [1S- (1α, 2α, 3α,4α) ]-2-[ [3-[[4-(pentylamine) carbonyl]-2-oxazolyl]-7-oxabicyclo [2.2.1] hept-2-yl]methyl]benzenepropanoic acid, sodium salt.

Methods

Male New Zealand white rabbits were euthanized by intravenous barbiturate overdose. The thoracic aorta and the left and right external jugular veins were then removed into warm (37° C.) physiological salt solution (PSS) of the following composition (mM): NaCl, 118.4; KCl, 4.7; $CaCl_2$, 2.5; $MgSO_4$, 1.2; $NaHCO_3$, 24.9; $KH_2PO_4$, 1.2; glucose, 11.1 and EDTA, 0.023; gassed with 95% $O_2$/5% $CO_2$, pH 7.4. The vessels were cleaned of fat and loose adventitia and subsequently cut into rings 3–4 mm in width. The endothelium was removed from the rings, unless otherwise indicated, by gently rotating a metal probe in the lumen of the ring. The rings were then suspended in water-jacketed (37° C.) 10 ml tissue baths between two wire holders, one of which was attached to a fixed hook and the other to an isometric force transducer. Resting tension was set at 4 g for the aorta and 1 g for the jugular vein. The venous tissues were allowed to stabilize for a period of one hour and then challenged with a maximally effective concentration of bradykinin (1 μM) to evoke a tonic contracture. This response was used as a comparative reference response. Carbachol (1 μM) was introduced into the bath following stabilization of the bradykinin contracture to test for the presence of endothelium. Failure to relax in response to carbachol indicated that the endothelium had been removed (tissues with an intact endothelium relaxed 50–100% upon exposure to carbachol). The tissues were washed multiple times with fresh PSS and allowed to recover for one hour following complete relaxation from the previous bradykinin response. At this time the tissues were challenged with increasing concentrations (cumulative addition) of CsA, Cremophor, ricinoleic acid or U-46,619 (11,9-epoxymethano-PGH$_2$) to establish a concentration-response relationship (one concentration-response curve per tissue). Inhibitors (enzyme or receptor) or their vehicle were introduced into the tissue bath 30 mins prior to the addition of stimulant. A similar procedure was followed for the aorta except the effects of carbachol (1 μM) were tested against a submaximal concentration of phenylephrine (0.3 μM) and 30 μM phenylephrine was used to establish a reference contracture.

CsA (Sandoz) was obtained as a 50 mg/ml solution (50 mg CsA dissolved in 650 mg Cremophor/32.9% alcohol) and was subsequently diluted in ethanol. Cremophor and ricinoleic acid (Sigma Chemical company) were also diluted in ethanol. The concentrations of CsA used were (μg/ml; final bath concentrations of Cremophor and ethanol are in parentheses ):0.3 (3.9 μg/ml, 0.1% ), 1.0 (13 μg/ml, 0.17%), 3.0 (39 μg/ml, 0.37%), 10 (130 μg/ml, 0.44%), 30 (390 μg/ml, 0.64%), 100 (1.3 mg/ml; 0.69%) and 300 (3.9 mg/ml; 0.82%). Cremophor was prepared by dilution in ethanol to yield final bath concentrations corresponding to those employed in the CsA experiments (i.e. 3.9 μg/ml Cremophor in 0.1% ethanol to 3.9 mg/ml Cremophor in 0.82% ethanol). Ricinoleic acid was diluted in ethanol to produce final bath concentrations of (μg/ml; final bath concentration of ethanol in parentheses): 0.1 (0.1%), 0.3 (0.3%), 1.0 (0.37%), 3.0 (0.57%), 10 (0.64%), 30 (0.84%). For reference, 0.1–30 μg/ml ricinoleic acid corresponds to a molar concentration range of 0.335–100.50 μM.

Force (mean±S.E.) is expressed as a percentage of the corresponding bradykinin or phenylephrine reference response. KB values were determined by Schild analysis and KBapp by the following formula: $K_{Bapp}$=[antagonist]/agonist concentration ratio-1, where agonist concentration ratio=agonist $EC_{50}$ measured in presence of antagonist/agonist $EC_{50}$ measured in presence of vehicle. The statistical significance between means was determined using Student's t-test with p<0.05 considered statistically significant.

Results

CsA-induced Force Development in the Jugular Vein (Cremophor Vehicle): Inhibition by Glyburide Cumulative addition of CsA, dissolved initially in Cremophor, resulted in a concentration-dependent increase in force (FIG. 1). CsA remained an equally efficacious activator of force in vessels in which the endothelium had been purposely left intact but exhibited a marginally, but significantly (p=0.01), reduced potency ($EC_{50}$ values: control 2.5±1.2 μg/ml; endothelium-intact 7.2±1.9 μg/ml, n=4 for both). The contractile response to CsA (5 μg/ml) was found to be partially reversed by the subsequent addition of glyburide; an inhibitor of both ATP-regulated potassium channels ($K_{ATP}$) and thromboxane $A_2$ receptors (Ashcroft "Adenosine 5'-triphosphate-sensitive potassium channels" Ann. Rev. Neurosci. 11:97–118, 1988; Cocks et al, "Glibenclamide is a competitive antagonist of the thromboxane $A_2$ receptor in dog coronary artery in vitro", Br. J. Pharmacol. 100:375–378, 1990). This inhibition was concentration-dependent with 57.1% inhibition occurring at 10 µM (n=2). Similarly, exposure to glyburide prior to and then during a subsequent challenge with increasing concentrations of CsA (cumulative addition) shifted the CsA concentration-response curve to the right in an approximately parallel fashion (FIG. 1; KB=0.6 µM, slope=0.7). Phentolamine (10 µM), which is also known to inhibit $K_{ATP}$ (McPherson and Angus, "Phentolamine and structurally related compounds selectively antagonize the vascular actions of the $K^+$ channel opener, cromakalim", Br. J. Pharmacol. 97:941–949, 1989), significantly affected neither the potency nor the maximal contractile effect of CsA ($EC_{50}$ values: control 2.5±1.2 µg/ml; phentolamine 2.0±1.0 µg/ml, n=4 for both).

Effect of Cremophor on Force Development in the Jugular Vein; Inhibition by Glyburide and the Thromboxane $A_2$/Prostaglandin Endoperoxide Receptor Antagonist BMS-180291

Figure 2:
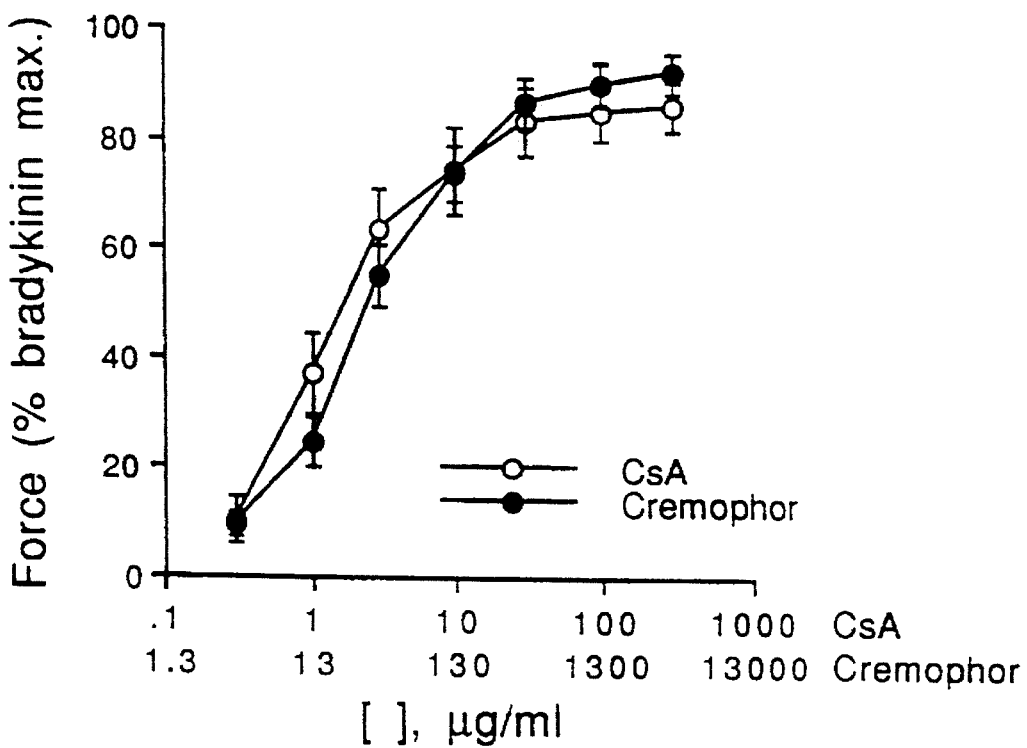
FIG. 2 is a graph showing comparative effects of CsA, dissolved in Cremophor (n=8), and Cremophor alone (n=12) on force development in the jugular vein. Force is expressed as a percentage of that generated by a maximally effective concentration of bradykinin.

Cumulative addition of Cremophor, the vehicle in which CsA was initially dissolved, also generated a concentration-dependent increase in force development ($EC_{50}$=39.5±10.9 µg/ml; FIG. 2). Given the direct vasoconstrictor effect of Cremophor it appears likely that Cremophor itself contributed to the apparent CsA-induced force development. A half maximal CsA response was achieved with a CsA concentration of 2.5±0.8 µg/ml (FIG. 2). The CsA solution contained 650 mg Cremophor per 50 mg CsA (see Methods) corresponding to 31.9±10.4 µg/ml Cremophor per 2.5±0.8 µg/ml CsA. This concentration of Cremophor is not significantly different from the concentration of Cremophor alone that was required to elicit 50% of maximal force (see above). Cremophor and CsA were also equally efficacious (FIG. 2). Thus, the observed CsA-induced force development appears to be due principally to the vasoconstrictor effects of its vehicle Cremophor.

Figure 3:
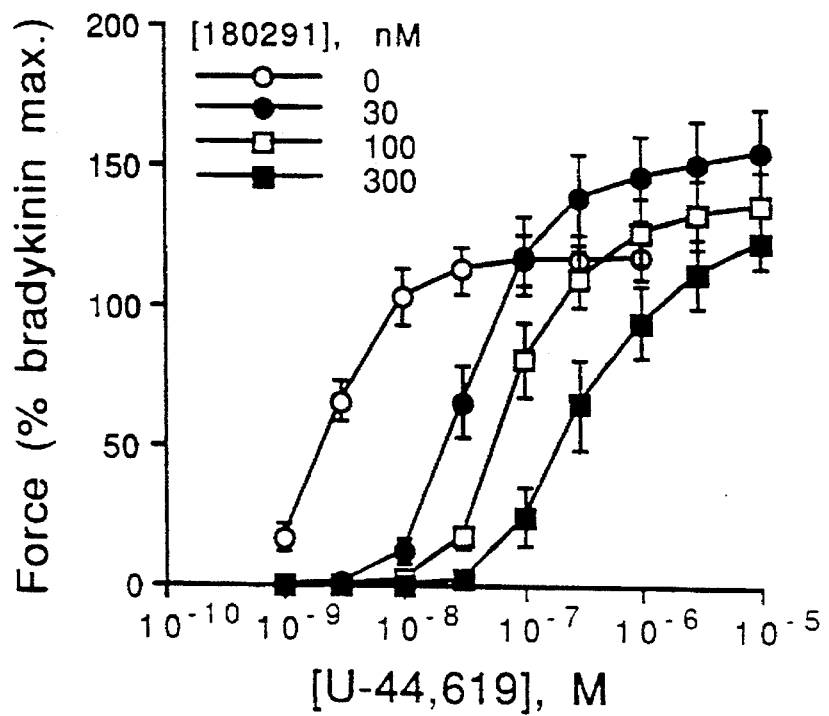
FIG. 3 is a graph showing effect of BMS-180291 on U-46,619-induced force in the jugular vein (n=4 for all groups). Force is expressed as a percentage of that generated by a maximally effective concentration of bradykinin.
Figure 4:
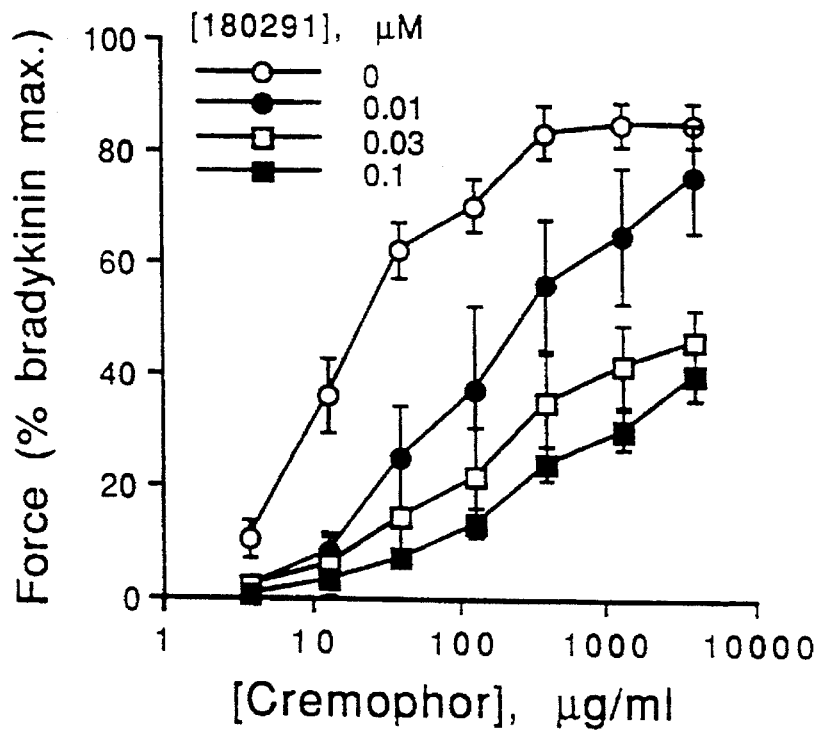
FIG. 4 is a graph showing effects of BMS-180291 on Cremophor-induced force development in the jugular vein (n=4–5 for all groups). Force is expressed as a percentage of that generated by a maximally effective concentration of bradykinin.

The Cremophor-induced contractile response, like that of CsA, was also antagonized by glyburide (10 µM). Moreover, the potency of glyburide as an antagonist of Cremophor-induced force was similar to that displayed against force evoked by CsA (KBapp: CSA 1.5 µM, n=4; Cremophor 0.9 µM, n=3). Cremophor-induced force development was also susceptible to inhibition by the thromboxane $A_2$ antagonist BMS-180291. BMS-180291 behaved as a competitive antagonist of U-46,619-induced force in rabbit jugular vein (FIG. 3:KB=3.6 nM, slope=1.0) and has previously been shown to competitively antagonize U- 46,619-induced force in both the rat (Ogletree et al, "Pharmacological profile of BMS 180,291: a potent, long-acting, orally active thromboxane $A_2$/prostaglandin endoperoxide receptor antagonist", J. Pharm. Exp. Ther. 264:570–578, 1993:KB=0.6 nM) and the rabbit aorta ($K_B$=4 nM; S. Moreland, unpublished). Rings of jugular vein that had been precontracted with Cremophor (39 µg/ml) relaxed 85.6±3.9% (n=4) upon the addition of 0.1 µM BMS- 180291. Similarly, preincubation of tissues with BMS- 180291 (10–300 nM) antagonized the subsequent Cremophor-induced responses, although in a fashion consistent with non-competitive antagonism (FIG. 4). Indomethacin (10 µM) failed to significantly inhibit the vasoconstrictor effects of Cremophor ($EC_{50}$ values: control 24.7±5.9 µg/ml, n=4; indomethacin 48.2±22.1 µg/ml, n=4).

Figure 5:
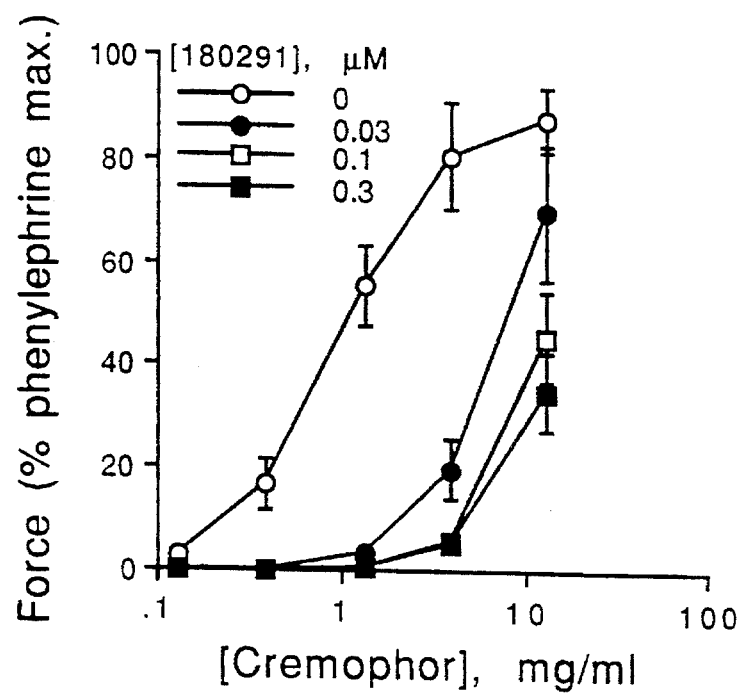
FIG. 5 is a graph showing effects of BMS-180291 on Cremophor-induced force development in the aorta (n=4 for each group). Force is expressed as a percentage of that generated by a maximally effective concentration of phenylephrine.

The vein also proved to be sensitive to the effects of ethanol, generating 24.1±3.3% (n=3) of the bradykinin reference force in response to the cumulative addition of 0.44% ethanol (FIG. 5). As a comparison 130 µg/ml Cremophor, which also contained 0.44% ethanol, produced 73.6±5.3% (n=12) of the reference bradykinin response (see FIG. 2). The contractile effects of ethanol, unlike those of Cremophor, were completely refractory to the subsequent addition of either 0.1 or 1 µM BMS-180291 (n=3).

Effects of Cremophor on Force Development in the Aorta: Antagonism by BMS180291

Cremophor also produced a concentration-dependent increase in force in the aorta but was found to be approximately 40 times less potent in this vessel ($EC_{50}$=1.5±0.5 mg/ml, n=5) than in the jugular vein (39.5±10.9 µg/ml, n=12). Cremophor-induced force in the aorta was also inhibited by BMS-180291 (FIG. 5). It was not possible to determine the maximally effective concentration of Cremophor in the presence of BMS-180291 because of the limited solubility of the Cremophor and the foaming of the Cremophor containing PSS at higher Cremophor concentrations. Thus, the nature of BMS-180291's antagonism of the Cremophor response is unclear. However, assuming a competitive antagonism, its $K_{Bapp}$ for the antagonism of Cremophor-induced force was 6.4 nM (based on 0.03 µM BMS-180291 only).

Effects of Ricinoleic Acid on Force Development in the Juaular Vein and Aorta: Antagonism by BMS-180291

Cremophor is a derivative of castor oil and ethylene oxide. Ricinoleic acid, the principal fatty acid in castor oil, produced concentration-dependent increases in force in both the vein (FIG. 6) and aorta (FIG. 7) but was approximately 20 times more potent in the vein ($EC_{50}$ values: vein 0.24±0.04 µg/ml, n=9; aorta 4.7±0.7 µg/ml, n=5). Furthermore, ricinoleic acid was found to be 165 times more potent than Cremophor in the vein and 326 times more potent in the aorta.

Figure 6:
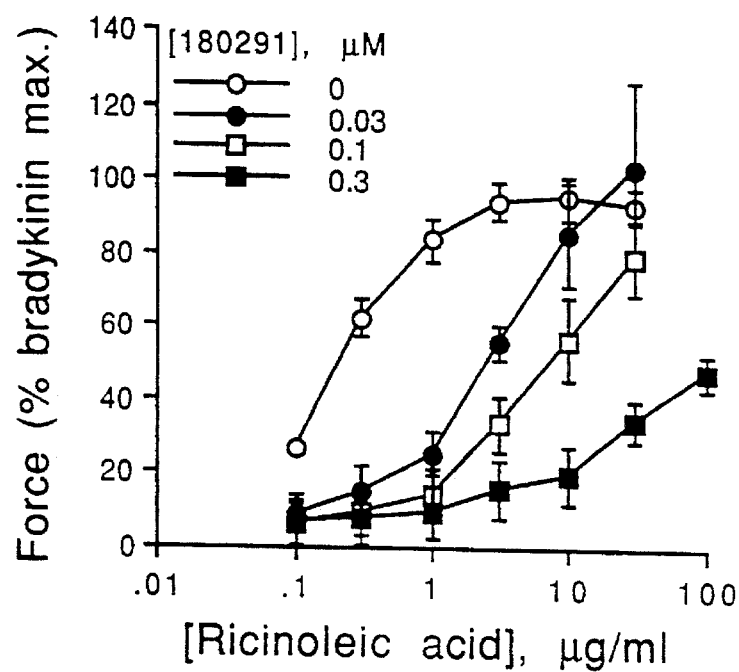
FIG. 6 is a graph showing effect of ricinoleic acid on force development in the jugular vein and its antagonism by BMS-180291 (n=4 for each group). Force is expressed as a percentage of that generated by a maximally effective concentration of bradykinin.
Figure 7:
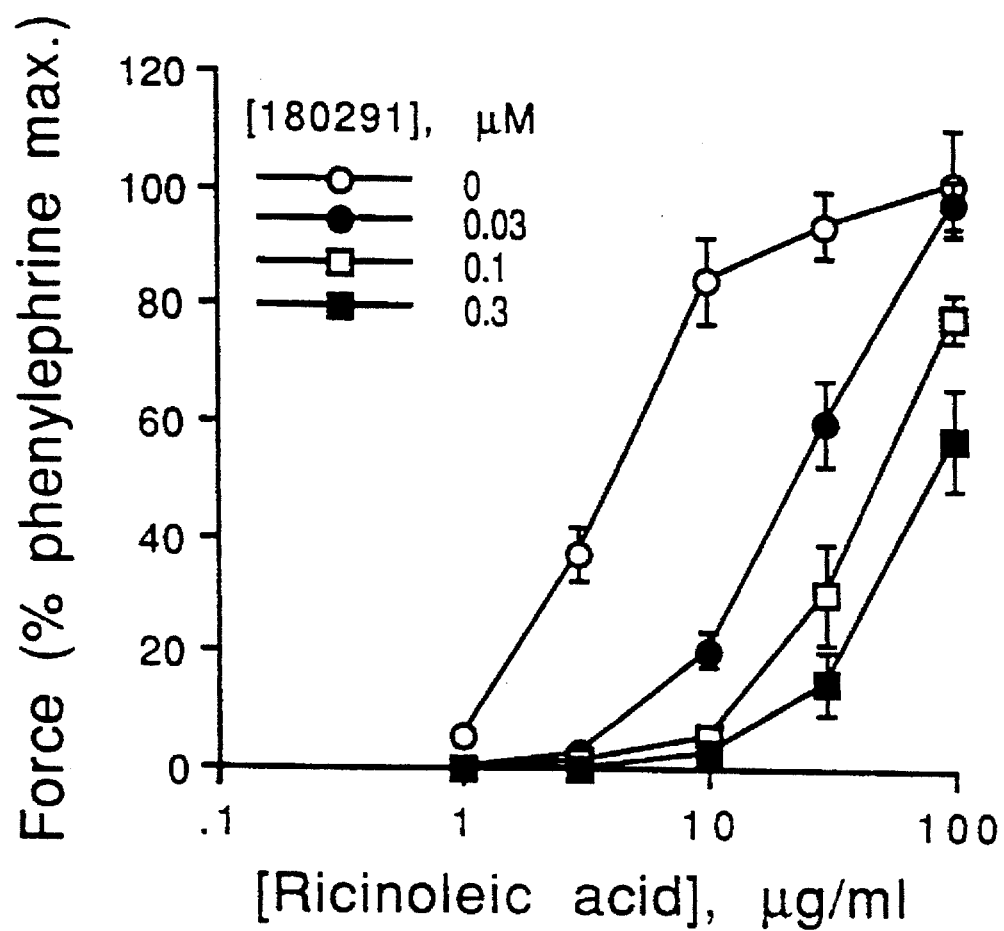
FIG. 7 is a graph showing effect of ricinoleic acid on force development in the aorta and its antagonism by BMS-180291 (n=4 for each group). Force is expressed as a percentage of that generated by a maximally effective concentration of phenylephrine.

The thromboxane $A_2$ receptor antagonist BMS- 180291 produced a concentration-dependent antagonism of the ricinoleic acid-induced force development in both preparations (FIGS. 6 and 7). Ricinoleic acid began to precipitate at concentrations of 100 µg/ml and higher and thus prevented the determination of the maximally effective concentration of ricinoleic acid at some BMS-180291 concentrations. However, if it is assumed that BMS-180291 and ricinoleic acid compete for the same site, a $K_{Bapp}$ Of 1.9 nM (based on 0.03 and 0.1 µM BMS-180291 only) may be determined for the vein and a $K_B$ of 4.3 nM (slope=0.70) for the aorta. Indomethacin, which was tested only in the vein, had no significant effect on ricinoleic acid-induced force ($EC_{50}$ values: control 0.17±0.05 µg/ml, n=4; indomethacin 0.40±0.11 µg/ml, n=4). Interestingly, ricinoleic acid was a weaker ($EC_{50}$>10 µM) and less efficacious (18.8±2.5% of maximum phenylephrine-induced response at 100 µg/ml ricinoleic acid) agonist in the rat aorta (n=4).

Discussion

CsA, dissolved in Cremophor vehicle, has previously been shown to increase the sensitivity of isolated blood vessels to various stimuli (Lamb and Webb, supra 1987). The present investigation extends these earlier findings and demonstrates that CsA, dissolved in Cremophor vehicle, directly evokes a concentration-dependent increase in force development in the rabbit jugular vein. The CsA-induced increase in force did not require the presence of an intact endothelium and was insensitive to phentolamine. The present data indicate that the rabbit jugular vein is more sensitive to the effects of CsA than either the rat tail artery where 10 µg/ml (8.3 µM) CsA had no direct effect on force or the rat portal vein where effects on frequency of contractions were first manifest at 3–10 µg/ml (Lamb and Webb, supra 1987).

Glyburide, an inhibitor of KATp (Longman and Hamilton, "Potassium channel activator drugs: mechanism of action, pharmacological properties and therapeutic potential", Medicinal Research Reviews 12:73–148, 1992), inhibited the vasoconstrictor effects of CsA in the jugular vein. Hence, it is possible that CsA may have evoked its contractile effect by activating $K_{ATP}$. However, it is difficult to envision how the opening of a potassium channel could lead to force development in a resting smooth muscle preparation. In addition, application of the potassium channel opener cromakalim is known to relax smooth muscle (Longman and Hamilton, supra 1992) and was found to evoke relaxation of CsA (3 µg/ml CsA)-induced force (present results). Lastly, the known $K_{ATP}$ inhibitor phentolamine (McPherson and Angus, supra 1989), failed to antagonize the effects of CsA. It appears likely, therefore, that another glyburide-sensitive mechanism might underlie the observed glyburide-induced inhibition of CsA-induced force. Cocks et al, supra (1990) have reported that glyburide behaves as a thromboxane $A_2$ receptor antagonist exhibiting a KB of 0.6 µM against this receptor. The present results show that glyburide antagonized CsA-induced force also with a $K_B$ of 0.6 µM, although with a slightly shallower slope (0.7) than would be expected for an ideal competitive antagonist. Thus it is hypothesized that the CsA evoked force development in the jugular vein occurred via the activation of thromboxane $A_2$ receptors and that these effects were inhibited by glyburide's action as a thromboxane $A_2$ receptor antagonist.

Cremophor, the vehicle in which CsA was initially dissolved, was also found to cause a concentration-dependent increase in force development in the vein. When the potency of Cremophor as a vasoconstrictor was compared with the concentration of Cremophor present in the CsA solutions it was apparent that the vasoconstrictor effects of CsA could mostly be accounted for by the constrictor effects of the Cremophor vehicle (FIG. 2). Ethanol was also found to constrict the vein and may have also contributed to the apparent Cremophor vehicle effects. Further support for the contention that the contractile effects of CsA were primarily mediated by the vehicle Cremophor was provided by the observation that glyburide was equally potent against both CsA and Cremophor-induced vasoconstriction (KBapp: CsA 1.5 µM; Cremophor 0.9 µM); it is also inferred that Cremophor's actions were themselves mediated via an interaction with thromboxane $A_2$ receptors.

BMS-180291, a potent thromboxane $A_2$/prostaglandin endoperoxide receptor antagonist (Ogletree et al, supra 1993), behaved as a potent ($K_B$=3.6 nM) and apparently competitive antagonist of U-46,619-induced force development in the jugular vein. The potency reported here is similar to that for U-46,619-induced force in the rat (Ogletree et al, supra 1993) and rabbit aorta (S. Moreland, unpublished). BMS-180291 also inhibited Cremophor-induced force in the vein, although in an apparently non-competitive fashion. Interestingly, previous studies have shown that BMS-180291, which antagonized U-46,619-evoked platelet shape change in an apparently competitive fashion, inhibited U-46,619-induced platelet aggregation in an apparently non-competitive fashion (Ogletree et al, supra 1993).

Cremophor, a derivative of castor oil and ethylene oxide, is principally composed of the triricinoleate ester of ethoxylated glycerol with smaller amounts of macrogol ricinoleate and the corresponding free glycols. Ricinoleic acid, the main fatty acid component (87%) of castor oil, evoked force development in the jugular vein ($EC_{50}$=0.24 µg/ml; 0.8 µM). The contractile effects of ricinoleic acid were antagonized by BMS-180291. Assuming this antagonism were of a competitive nature, the potency of BMS-180291 ($K_{Bapp}$=1.9 nM) against ricinoleic acid suggests that the vasoconstrictor effects of this fatty acid were mediated by thromboxane $A_2$ receptors. It also appears plausible that the ricinoleic acid-derived component of Cremophor may have mediated the thromboxane $A_2$ agonist actions of the Cremophor. The reduced potency exhibited by Cremophor relative to ricinoleic acid indicates that the derivative of ricinoleic acid that exists in Cremophor is less potent as a thromboxane agonist than the parent fatty acid. It is also possible that the vasoconstrictor effects of Cremophor are mediated by a small amount of free ricinoleic acid that may have existed in the Cremophor; 0.6% by volume would be sufficient. The contractile effects of neither ricinoleic acid nor Cremophor were prevented by the cyclooxygenase inhibitor indomethacin, indicating that both substances behaved as direct agonists rather than substrates for the production of thromboxane $A_2$.

In a comparative study employing the rabbit aorta, both Cremophor ($EC_{50}$=1.5 µg/ml) and ricinoleic acid ($EC_{50}$=4.7 µg/ml) were found to be less potent than in the jugular vein. However, consistent with the vein, responses to both stimuli were antagonized by BMS-180291. Assuming competitive antagonism, the potency of BMS-180291 against both the Cremophor ($K_{Bapp}$=6.4 nM) and ricinoleic acid ($K_B$=4.3 nM) responses is consistent with an antagonism of thromboxane $A_2$ receptors. The rat aorta was also considerably less sensitive to the effects of ricinoleic acid than either the vein or the rabbit aorta. It is plausible, therefore, that the ricinoleic acid receptor (presumably thromboxane $A_2$) is not identical in these vascular preparations. In contrast, U-46, 619 is of approximately equal potency in all three tissues (present study; Ogletree et al, supra 1993; S. Moreland, unpublished).

The therapeutically useful concentration of CsA in renal transplant patients is in the range of 95–205 to 250–500 ng/ml whole blood, when assayed by monoclonal or polyclonal antibody assays, respectively (Kwan et al, "Therapeutic range of cyclosporin in renal transplant patients by specific monoclonal radioimmunoassay", Lancet ii:962–963 1987). If this concentration of CsA were achieved by intravenous dosing and it is assumed that the CsA/Cremophor ratio remains constant, the CsA would carry with it 1.2–6.5 µg/ml Cremophor. Given the in vitro potency of Cremophor as a direct vasoconstrictor, it appears likely that the Cremophor would only produce a small increase in venous tone. Nevertheless, even a partial increase in vascular tone in response to Cremophor may amplify the responsiveness of that vessel to other stimuli. A further complication in the extrapolation of in vitro data to clinical outcome is the potential for considerable species and blood vessel differences in the potency of Cremophor as a thromboxane $A_2$ agonist; exemplified by a comparison of the potency of CsA in the rabbit jugular vein with previous results in isolated rat vessels (Lamb and Webb, supra 1987). Species and blood vessel differences are also apparent from the present findings that ricinoleic is a weaker and less efficacious agonist in the rat aorta than the rabbit aorta and that both Cremophor and ricinoleic acid are far more potent in the jugular vein than in the aorta.

In summary, CsA evoked force development in the rabbit jugular vein appears to be mediated primarily by the action of its vehicle, Cremophor. It appears that Cremophor evoked force development by acting as a weak thromboxane $A_2$ agonist. Ricinoleic acid was also found to behave as a weak thromboxane $A_2$ agonist. Thus, it appears that the ricinoleic acid-derivative found in Cremophor, or a small amount of free ricinoleic acid, mediates Cremophor's interaction with thromboxane $A_2$ receptors.

What is claimed is:

1. A method for inhibiting, treating or reducing unwanted side effects caused by a pharmaceutical solvent containing ricinoleic acid or castor oil or a derivative thereof, wherein said derivative is selected from the group consisting of Cremopor, Cremophor EL, polyoxl 35 castor oil, polyethoxylated castor oils, triricinoleate ester of ethoxylated glycerol with macrogol ricinoleate and the corresponding free glycerols, which comprises employing a thromboxane $A_2$ receptor antagonist in conjunction with such solvent.

2. The method as defined in claim 1 wherein said derivative is Cremophor.

3. The method as defined in claim 1 wherein said derivative is the triricinoleate ester of ethoxylated glycerol with the corresponding free glycerols.

4. The method as defined in claim 1 wherein the thromboxane $A_2$ receptor antagonist is employed in conjunction with a pharmaceutical composition including a pharmaceutical and the solvent containing ricinoleic acid or castor oil or a derivative thereof.

5. The method as defined in claim 4 wherein the pharmaceutical composition includes a pharmaceutical which is cyclosporine A, vitamin K, taxol, teniposide, didemnin B, miconazole, diazepam, althesin, or echinomycin.

6. The method as defined in claim 5 wherein the pharmaceutical composition includes cyclosporine A in Cremophor EL.

7. The method as defined in claim 1 wherein the thromboxane $A_2$ receptor antagonist is employed in a weight ratio to the solvent of within the range of from about 0.0001:1 to about 10.000:1.

8. The method as defined in claim 4 wherein the thromboxane $A_2$ receptor antagonist is employed in a weight ratio to the pharmaceutical of within the range of from about 0.0001:1 to about 500:1.

9. The method as defined in claim 1 wherein the thromboxane $A_2$ receptor antagonist is [1S-[ 1α,2α, (Z),3α(1E, 3S*,4R*) ,4α]]-7-[3-(3-hydroxy-4-phenyl- 1-pentenyl)-7-oxabicyclo [2.2.1]hept-2-yl]-5-heptenoic acid (SQ 29,548); [1S- [1α, 2α(Z), 3α, 4α]]-7-[ 3-[[2- (phenyl-amino) carbonyl]hydrazino]methyl]-7-oxabicyclo[ 2.2.1] -hept-2-yl]-5-heptenoic acid;[1S-[ 1α, 2α(Z),3α, 4α]]-7-[3-[[[(1-oxoheptyl)amino]-acetyl] amino]methyl]-7 -oxabicyclo [2.2.1] hept-2-yl]-5-heptenoic acid (SQ30,741) and the corresponding tetrazole, and [1S-[1α,2α(Z),3α,4α]]-7-[3-[[[[(4-cyclohexyl- 1-oxobutyl)amino]acetyl]amino]methyl]-7-oxabicyclo-[ 2.2.1]hept-2-yl]-5-heptenoic acid; [1S-[ 1α,2α,3α, 4α)]-2-[[3-[[4-(pentylamino)carbonyl]-2-oxazolyl] -7-oxabicyclo [2.2.1]hept-2-yl]methyl]-benzenepropanoic acid, sodium salt referred to as BMS 180,291 herein, or esters or other salts thereof, [1S-(1α,2α,3α,4α)]-2-[[3-[4-[ [(4-cyclohexylbutyl)-amino] carbonyl]-2-oxazolyl]-7-oxabicyclo[2.2.1]hept- 2-yl]methyl]benzenepropanoic acid, (SQ 33,961); [1S(1α,2α,3α,4α)] -2-[[3-[4-[[[(4-chlorophenyl)butyl-amino] carbonyl]-2-oxazolyl]-7-oxabicyclo[ 2.2.1] hept-2-yl] methyl]benzenepropanoic acid or esters, or salts thereof; [1S-(1α,2α,3α,4α)]-3-[[3-[ 4-[[(4-cyclohexylbutyl) amino]carbonyl ]-2-oxazolyl]- 7-oxabicyclo[2.2.1] hept-2-yl]methyl]benzeneacetic acid, or esters or salts thereof; [1S-( 1α,2α,3α,4α)]-2-[[3-[4-[[(4-cyclohexylbutyl) amino] -carbonyl] -2-oxazolyl]-7-oxabicyclo [2.2.1]hept-2y-l] methyl]phenoxy]acetic acid, or esters or salts thereof; [1S- (1α,2α,3α, 4α)] -2- [[3- [4- [[(7,7-dimethyloctyl ) amino]carbonyl]-2-oxazolyl]-7-oxabicyclo [2.2.1]hept -2-yl]methyl]benzenepropanoic acid, or esters or salts thereof; [1S-[ 1α,2α(Z),3α,4α]]-6-[3-[4-[[(4-cyclohexylbutyl)-amino] carbonyl] -2-oxazolyl]-7-oxabicyclo [2.2.1] hept- 2-yl]-4-hexenoic acid, or esters or salts thereof; [1S-[1α, 2α(Z), 3α,4α]] -6- [3- [4- [[(4-cyclohexylbutyl)-amino] carbonyl]-2-thiazolyl]-7-oxabicyclo [2.2.1]hept-2-yl]-4-hexenoic acid, or esters or salts thereof; [1S- [1α, 2α(Z), 3α,4α]]-6-[3-[4-[[(4-cyclohexylbutyl)-methylamino] carbonyl] -2-oxazolyl]-7 -oxabicyclo-[ 2.2.1] hept-2-yl]-4-hexenoic acid, or esters or salts thereof; [1S-[1α, 2α(Z),3α,4α]]-6-[3-[4-[(1-pyrrolidinyl) carbonyl] -2-oxazolyl]-7-oxabicyclo-[ 2.2.1]hept-2-yl]-4-hexenoic acid, or esters or salts thereof; [1S-[1α, 2α(Z),3α,4α]]-6-[3-[4-[ (cyclohexylamino)-carbonyl]-2-oxazolyl]-7-oxabicyclo [2.2.1] hept-2-yl]-4-hexenoic acid or esters or salts thereof; [ 1S- [1α, 2α(Z) , 3α,4α]] -6-[3-[4-[ [(2-cyclohexylethyl) amino]carbonyl]-2-oxazolyl]-7-oxabicyclo [2.2.1] hept-2-yl] -4-hexenoic acid, or esters or salts thereof; [1S-[1α, 2α(Z),3α4α]]-6-[3-[ 4-[[[2 (4-chlorophenyl)ethyl]amino] carbonyl]-2-oxazolyl] -7-oxabicyclo [2.2.1]hept-2-yl]-4-hexenoic acid, or esters or salts thereof; [1S-[ [1α,2α(Z), 3α,4α]]-6-[3-[4-[[(4-chlorophenyl)amino]-carbonyl] -2-oxazolyl]-7-oxabicyclo [2.2.1]hept -2-yl]- 4-hexenoic acid, or esters or salts thereof; [1S1α,2α(Z), 3α, 4α]]-6-[3-[4-[[[4-(4-chlorophenyl)-butyl] amino]carbonyl]-2-oxazolyl]-7-oxabicyclo-[ 2.2.1]hept-2-yl]-4-hexenoic acid, or esters or salts thereof; [1S-[1α, 2α(Z), 3α,4α]]-6-[3-[4a-[[(6-cyclohexylhexyl) amino]carbonyl] -2-oxazolyl]-7-oxabicyclo [2.2.1] hept-2-yl]-4-hexenoic acid, or esters, or salts thereof; [1S-[1α,2α(E),3β,4α]]-6-[3-[ 4-[[(6-cyclohexylhexyl)amino] carbonyl]-2-oxazolyl]- 7-oxabicyclo[2.2.1] hept-2-yl] -4-hexenoic acid, or esters or salts thereof; [1S-[1α,2α(Z), 3α,4α]]-6-[3-[ 4-[(propylamino)carbonyl] -2-oxazolyl]-7-oxabicyclo-[ 2.2.1]hept-2-yl]-4-hexenoic acid, or esters or salts thereof; [1S-[1α,2α(Z) ,3α,4α]]-6-[3-[4-[[(4-butylphenyl) amino]carbonyl]-2-oxazolyl]-7-oxabicyclo -[2.2.1] hept-2-yl]-4-hexenoic acid, or esters or salts thereof; [1S-[1α,2α(Z) ,3α,4α]]-6-[3-[4-[(2,3-dihydro- 1H-indol-1yl) carbonyl]-2-oxazolyl]-7-oxabicyclo [2.2.1] hept-2-yl]-4-hexenoic acid, or esters or salts thereof; [1S-[1α,2α(Z),3α, 4α]]-6-[3-[ 4-[[(4-cyclohexylbutyl)amino]carbonyl]-2-oxazolyl]- 7-oxabicyclo [2.2.1] hept-2-yl]-N-(phenylsulfonyl) -4-hexenamide; [1S- [1α,2α(Z), 3α, 4α]]-6-[3-[4-[[(4-cyclohexylbutyl) amino]carbonyl]-2-oxazolyl]-N-(methylsulfonyl)- 7-oxabicyclo [2.2.1]hept-2-yl ]-4-hexenamide; [1S-[1α,2α(Z),3α,4α]]-7-[3-[4-[[(4-cyclohexylbutyl) amino] carbonyl]-2-oxazolyl]-7-oxabicyclo [2.2.1] hept-2-yl]-5-heptenoic acid, or esters or salts thereof; [1S-[1α,2α(Z),3α, 4α]]-6-[3-[ 4-[[(4-cyclohexylbutyl)amino]carbonyl]-1H-imidazol- 2-yl]-7-oxabicyclo[2.2.1]hept-2-yl]-4-hexenoic acid or esters or salts thereof; [1S-[1α,2α,3α,4α]]-6-[3-[ 4-[[(7,7-dimethyloctyl)amino]carbonyl]-2-oxazolyl]- 7-oxabicyclo[2.2.1] hept-2-yl]-4-hexenoic acid, or esters or salts thereof; [1S-[1α,2α(Z),3α,4α]]-6-[3-[ 4-[[(4-cyclohexylbutyl)amino]carbonyl] -2-oxazolyl]-7-oxabicyclo[2.2.1]hept-2-yl]-4-hexenoic acid; (1S-[1α,2α,3α,4α]]-3-[4-[[(4-cyclohexylbutyl) amino]-carbonyl] -2-oxazolyl]-7-oxabicyclo [2.2.1]heptane-2-hexenoic acid or esters or salts thereof, [1S-[ 1α,2αZ, 3α, 4α]]-6-[3- [4-[[[(4-cyclohexylbutyl)- amino] carbonyl] -2-oxazolyl]-7-oxabicyclo [2.2.1]hept-2-yl]-4-hexenoic acid or esters or salts thereof; [1S- [1α, 2α(Z), 3α, 4α]]-6-[3- [ [4-(4-cyclohexyl-1-hydroxybutyl) -1H- imidazol-1-yl]methyl]-7-oxabicyclo [2.2.1] hept-2-yl] -4-hexenoic acid or its methyl ester; [1S-[1α, 2α(Z),3α,4α] ]-6-[3-[[4-(3-cyclohexypropyl) -1H-imidazol-1-yl]methyl]-7-oxabicyclo [2.2.1]hept-2-yl] -4-hexenoic acid or its methyl ester; [1S-[1α,2α(Z),3α,4α]]-6-[3-[[4-(4-cyclohexyl -1-oxobutyl)-1H-imidazol-1-yl]methyl]-7-oxabicyclo [2.2.1] hept-2-yl] -4-hexenoic acid or its methyl ester; [1S-[1α,2α(Z),3α,4α]]-6-[3-(1H-imidazol- 1-ylmethyl]-7-oxabicyclo [2.2.1]hept -2-yl]-4-hexenoic acid or its methyl ester; or [1S-[ 1α, 2α(Z),3α,4α(Z)]-6-[3-[[4-[[(4-cyclohexylbutyl)-amino] carbonyl]-1H-imidazol-1-yl]methyl]-7-oxabicyclo [2.2.1] hept-2-yl] -4-hexenoic acid or its methyl ester; 4-[2-(benzenesulfamido)ethyl]phenoxyacetic acid (BM 13,177; 4-[2-(4-chlorobenzene-sulfonamido)ethyl] phenylacetic acid (BM 13,505); 4-( 3-((4-chlorophenyl)sulfonyl)propyl) benzeneacetic acid; (E) -5-[[[(pyridinyl)[3-(trifluoromethyl)-phenyl] methylene]amino]oxy]pentanoic acid; (R68,070) 3-[1-(4-chlorophenylmethyl)-5-fluoro-3-methylindol-2-yl]-2,2-dimethylpropanoic acid (L-655240), 5 (Z) -7-( 2,4,5-cis)-4-(2-hydroxyphenyl)-2-trifluoromethyl-1,3-dioxan-5-yl)heptenoic acid (ICI 185282); 5 (Z) -7-[ 2,2-dimethyl-4-phenyl-1,3-dioxan-cis-5-yl]heptenoic acid (ICI 159995); N,N'-bis[7-(3-chlorobenzeneamino-sulfonyl)-1,2,3,4-tetrahydro-isoquinol-yl]disulfonylimide (SKF 88046); [1α(Z)-2β,5α]-(+)-7-[5-[[(1,1'-biphenyl)- 4-yl]-methoxy]-2-(4-morpholinyl)-3-oxocyclopentyl] -4-heptenoic acid (AH 23848); levallorphan allyl bromide (CM 32,191); (Z,2-endo-3-oxo)- 7-(3-acetyl-2-bicyclo[2.2.1] -heptyl-5-hepta-3Z-enoic acid, 4-phenylthiosemicarbazone (EP092); GR 32,191- 8 1R-[1α(Z),2β,3β,5α]]-(+)-7-[5-([1, 1'-biphenyl] -4-ylmethoxy)-3-hydroxy-2-(1-piperidinyl)-cyclopentyl] -4-heptenoic acid; ICI 192,605-4 (Z)-6-[ (2,4,5-cis)2-chlorophenyl)-4-(2-hydroxyphenyl)1,3-dioxan- 5-yl] hexenoic acid; BAY u 3405- 3-[[(4-fluorophenyl)sulfonyl] amino]-1,2,3,4-tetrahydro-9H-carbazole- 9-propanoic acid; or ONO 3708-7-[2α,4α-(di-methyl-methano)- 6β-(2-cyclopentyl-2β-hydroxyacetamido)-1α-cyclohexyl]-5(Z)-heptenoic acid; (±) (5Z)-7-[3-endo-[(phenylsulfonyl)amino]bicyclo-[ 2.2.1]hept-2-exo-yl]heptenoic acid (S-145, Shionogi); (−)6,8-difluoro-9-p-methylsulfonylbenzyl- 1,2,3, 4-tetrahydrocarbazol-1-yl-acetic acid (L670596, Merck) and (3-[1-(4-chlorobenzyl)-5-fluoro-3-methyl-indol- 2-yl]2,2-dimethylpropanoic acid (L655240, Merck), and glyburide.

10. The method as defined in claim 9 wherein the thromboxane $A_2$ receptor antagonist is BMS 180,291.

\* \* \* \* \*